(12) United States Patent
Hsu et al.

(10) Patent No.: US 8,900,843 B2
(45) Date of Patent: Dec. 2, 2014

(54) KIT AND METHOD FOR THE CAPTURE OF TUMOR CELLS

(71) Applicant: Taipei Medical University, Taipei (TW)

(72) Inventors: Fang-Chi Hsu, Taipei (TW); Richard Li-Chern Pan, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 14/212,995

(22) Filed: Mar. 14, 2014

(65) Prior Publication Data

US 2014/0199748 A1 Jul. 17, 2014

Related U.S. Application Data

(62) Division of application No. 12/649,026, filed on Dec. 29, 2009, now Pat. No. 8,709,801.

(51) Int. Cl.
*C12N 11/02* (2006.01)
*C12N 5/09* (2010.01)
*C12N 5/071* (2010.01)

(52) U.S. Cl.
CPC .......... *C12N 5/0693* (2013.01); *C12N 2502/28* (2013.01); *C12N 2502/30* (2013.01); *C12N 5/0697* (2013.01)
USPC .......................................... 435/177; 435/174

(58) Field of Classification Search
None
See application file for complete search history.

*Primary Examiner* — Kade Ariani
(74) *Attorney, Agent, or Firm* — WPAT, P.C.; Anthony King

(57) ABSTRACT

The invention relates to a kit and method for the capture of tumor cells in a body fluid sample. The kit and method of the invention can capture living tumor cells but not non-living tumor cells or cell fragments so that the tumor species can be further identified by further culture of the captured tumor cells. Also, the kit and method of the invention can readily identify whether a sample contains tumor cells and collect these tumor cells for further identification so that the presence of cancer and development of the metastasis and early relapse can be found.

18 Claims, 4 Drawing Sheets

(A)

(B)

(A)

(B)

KIT AND METHOD FOR THE CAPTURE OF TUMOR CELLS

FIELD OF THE INVENTION

The invention relates to a kit and method for the capture of tumor cells in a body fluid sample or a serum-containing sample. Particularly, the kit and method of the invention are provided to capture circulating tumor cells.

BACKGROUND OF THE INVENTION

Cancer is caused by cumulative multiple genetic mutations, which result in the activation of oncogenes and/or the inactivation of tumor suppressor genes. Cancer remains a major cause of mortality worldwide. Despite advancements in diagnosis and treatment, the overall survival rate has not improved significantly in the past several years. There remains an unfulfilled need for more accurate detection and sensitive means of diagnosis of tumors.

Most cancer deaths are not caused by the primary tumor. Instead, death results from metastases, i.e., multiple widespread tumor colonies established by malignant cells that detach themselves from the site of the original tumor and travel through the body, often to distant sites. If a primary tumor is detected early enough, surgery, radiation, chemotherapy, or some combination of these treatments can often eliminate it. Unfortunately, the metastatic colonies are harder to detect and eliminate and it is often impossible to treat all of them successfully. Therefore, from a clinical point of view, metastasis can be considered as the conclusive event in the natural progression of cancer. Moreover, the ability to metastasize is the property that uniquely characterizes a malignant tumor. Cancer metastasis comprises the following complex series of sequential events: 1. Extension from the primary locus into surrounding tissues; 2. Penetration into body cavities and vessels; 3. Release of tumor cells for transport through the circulatory system to distant sites; 4. Re-invasion of tissue at the site of arrest; and 5. Adaptation to the new environment so as to promote tumor cell survival, vascularization, and tumor growth. Due to the complexity of cancer and cancer metastasis, and frustration resulting from the lack of effective treatment for late-stage cancer patients, much effort has been invested in developing tests to detect development of metastasis and early relapse.

Circulating tumor cells (CTCs) are cancer cells that are shed from either the primary tumor or its metastases and that circulate in the peripheral blood. While metastases are directly responsible for the majority of cancer deaths, CTCs may constitute seeds for metastases and may indicate the spread of the disease. The ability to identify CTCs when they are very sparse (at most a few CTCs per ml) could allow early detection of indications of a cancer, or even of a precancerous growth before the appearance of evident clinical symptoms. Potential interest in detection of CTCs in peripheral blood was first suggested over a century ago, but then subsided because they are difficult to detect by conventional methods due to low numbers of CTCs in a sample. The challenge is to develop an approach that is capable of both highly sensitive and highly specific identification and characterization of rare tumor cells circulating in the blood, enabling such cells to be distinguished from normal epithelial cells and leukocytes. Detection of circulating tumor cells could facilitate cancer prognosis, diagnosis of minimal residual disease, assessment of tumor sensitivity to anticancer drugs, and personalization of anticancer therapy. Highly sensitive and specific identification of CTCs would also have potential application in early diagnosis and screening of invasive cancers.

Molecular techniques based on PCR amplification of tumor-specific abnormalities in DNA or RNA have facilitated detection of occult (hidden) tumor cells. PCR-based tests capable of routinely detecting one tumor cell in one million normal cells have been devised for identification of circulating tumor cells in various types of carcinomas. For example, Smith B. et al. develops reverse transcriptase-polymerase chain reaction to detect melanoma cells in peripheral blood (Lancet, 338: 1227-1236, 1991). However, these methods may not effectively distinguish viable tumor cells from normal cells. Since cell integrity is destroyed during DNA or RNA extraction, this approach precludes the analysis of cell morphology and phenotype, and so may be unable to distinguish material shed directly from normal tissue as opposed to from tumors, nor allow detection of several associated changes in the same cell.

Immunofluorescence microscopy enables analysis of cell morphology and direct counting of identifiable presumptive tumor cells. Detection is carried out by immunolabeling of cells using appropriate antibodies. However, there are so far no antibodies for tumor specific antigens used to identify CTCs. In addition, immunomagnetic cell separation with immunocytochemical labeling has been developed and evaluated for detection of CTC clusters in colorectal carcinoma patients (Clinical Cancer Research, 2001, Vol. 7, pp.4080-4085). WO 2006050352 provides an improved cell adhesion matrix ("CAM") and an improved cell isolation device for separating target cells such as tumor, fetal and angiogenic cells from blood or other fluid tissue samples. Furthermore, WO 2009051734 discloses a device for capturing circulating, nonhemopoietic tumor cells. The device includes a microfluidic channel to which is bound a tumor specific binding agent; and a pump producing a continuous, unidirectional shear stress of 0.1 to 20 dyn/cm$^2$ in the channel. However, the above techniques cannot effectively detect CTC.

It is apparent that there is need for a method and/or kit for identifying cells in circulation having metastatic potential prior to establishment of a secondary tumor, particularly during the early stages of cancer.

SUMMARY OF THE INVENTION

One object of the invention is to provide a method for capture of tumor cells in a body fluid sample or a serum-containing sample, comprising the following steps:
(a) attaching endothelium-like or epithelium-like cells on a solid support,
(b) inducing an inflammatory reaction of the cells of (a) with one or more inflammation-inducing agents;
(c) attaching white blood cells to the cells of (a); and
(d) adding a body fluid sample or a serum-containing sample to the solid support whereby the white blood cells of (c) and the endothelium-like or epithelium-like cells of (a) capture tumor cells contained in the body fluid sample or the serum-containing sample.

Another object of the invention is to provide a kit for capture of tumor cells in a body fluid sample or a serum-containing sample, comprising (a) a solid support; (b) endothelium-like or epithelium-like cells that are attached on the solid support; (c) white blood cells that are attached to the cells of (b); and (d) one or more inflammation-inducing agents.

BRIEF DESCRIPTION OF THE DRAWING

FIG. 3(A) is a control group wherein no white blood cells were added. The "a" in the figure represents tumor cells (hepG2 cells); the "b" represents epithelium cells; and the "c" represents white blood cells (neutrophils).

DETAILED DESCRIPTION OF THE INVENTION

Figure 1:
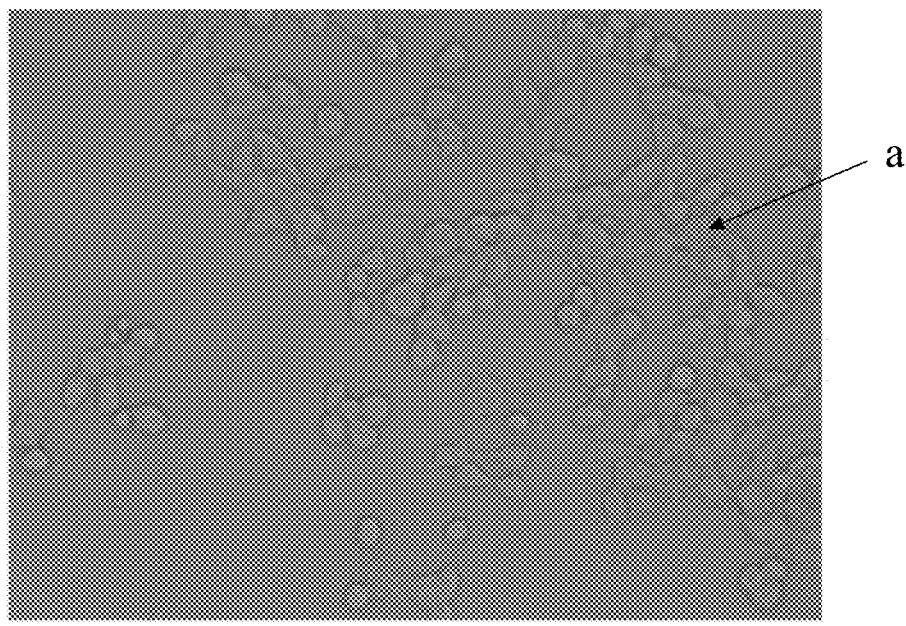
FIG. 1 is directed to optical microscope photographs showing the attachment of tumor cells to the epithelium cells either with (B) or without (A) inducing an inflammation reaction on the epithelium cells by using IL-1β. The "a" in the figure represents tumor cells (hepG2 cells) and the "b" represents epithelium cells.
Figure 1:
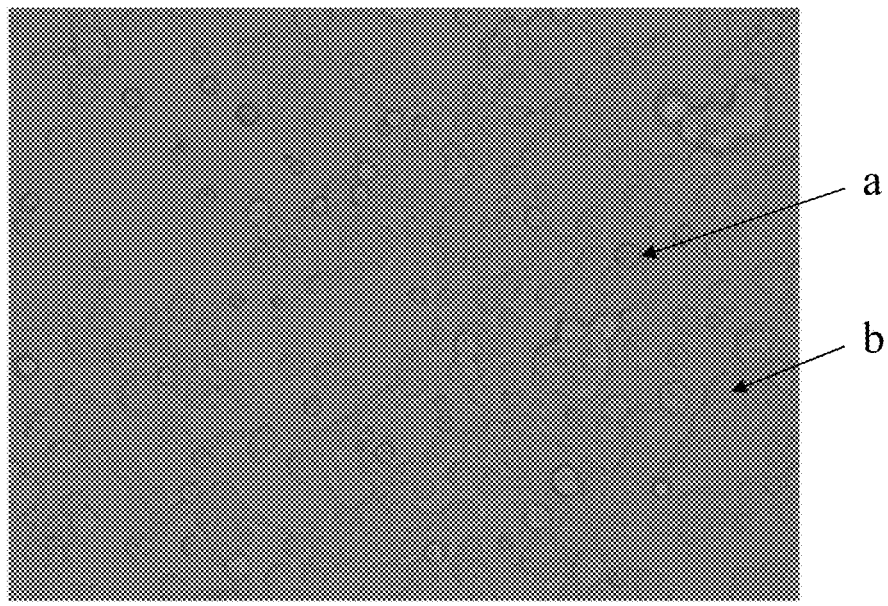

This invention relates to a method and kit for capturing tumor cells in a body fluid sample or a serum-containing sample. The detection and confirmation of tumor cells in the body fluid sample or the serum-containing sample can be achieved by utilizing the concept that white blood cells can capture living, nucleus-containing heterogenic cells in a sample. The kit and method of the invention can capture living tumor cells but not non-living tumor cells or cell fragments, so that the tumor species can be further identified by further culture of the captured tumor cells. It is difficult to identify unknown tumor cells in a test sample because they are rare and have various size and epitope. The kit and method of the invention can readily identify whether a sample contains tumor cells and collect these tumor cells for further identification so that the presence of cancer and development of the metastasis and early relapse can be identified.

In one aspect, the invention provides a method for capture of tumor cells in a body fluid sample or a serum-containing sample, comprising the following steps:
(a) attaching endothelium-like or epithelium-like cells on a solid support,
(b) inducing an inflammatory reaction of the cells of (a) with one or more inflammation-inducing agents;
(c) attaching white blood cells to the cells of (a); and
(d) adding a body fluid sample to the solid support whereby the white blood cells of (c) and the endothelium-like or epithelium-like cells of (a) capture tumor cells contained in the body fluid sample or the serum-containing sample.

In one embodiment, the method can further comprise a step of pre-treating the body fluid sample or serum-containing sample prior to use so that the sample is in a physiological condition. In another embodiment, the method can further comprise, a step of pre-treating a biological sample to form a body fluid sample or a serum-containing sample prior to use.

In further another embodiment, the method can also further comprise a step of harvesting the captured tumor cells after step (d).

In another aspect, the invention provides a kit for the capture of tumor cells in a body fluid sample or a serum-containing sample, comprising (a) a solid support, (b) endothelium-like or epithelium-like cells that are attached on the solid support, (c) white blood cells that are attached to the cells of (b), and (d) one or more inflammation-inducing agents.

According to the invention, the "solid support" or "solid carrier" means any solid phase material upon which the cells used in the capture of the invention can be attached, ligated or immobilized. Solid support encompasses terms such as "membrane," "resin;" "solid phase," "surface" and "support." In one embodiment, the solid support is hydrophilic. Particularly, the surface of the solid support can be modified to be hydrophilic. The process for the modification can be, but is not limited to, oxygen plasma, water plasma and chemical treatment. This support may be composed of organic polymers such as nitrocellulose membrane, nylon membrane, polystyrene, polyethylene, polypropylene, polyfluoroethylene, polyethyleneoxy, and polyacrylamide, as well as co-polymers and grafts thereof. The solid support may also be inorganic, such as glass, silica, reverse-phase silica or a bio-chip. The configuration of the solid support may be in the form of beads, spheres, particles, granules, gel, or surface. Surfaces may be planar, substantially planar, or non-planar. The solid support may be configured in the form of a well, depression or other container, vessel, feature or location. Preferably, the solid support is a Petri dish or plate, preferably with a plurality of wells in which an assay can be conducted. Preferably, the plate is a multi-well microtiter plate. In another embodiment, the surface of the support can have an electrode(s). The electrode(s) can detect the presence of the captured tumor cells and their amount. Detection of cells with electrodes is known in the art. U.S. Pat. No. 6,716,633 provides a blood cell detector including an orifice section having a single orifice, a first supplying section for supplying a first blood specimen into the orifice section, a second supplying section for supplying a second blood specimen into the orifice section, and first and second electrodes provided on opposite sides of the orifice for detecting a change in impedance of each of the first and second blood specimens when the first and second blood specimens are selectively caused to pass through the orifice, and the reference is incorporated herein by reference. In one embodiment, the electrode can be composed of indium tin oxide (ITO), carbon nanotube, silicon, or titanium oxide. The electrode can produce dielectrophorestic force (DEP Force) by change of electric current frequency. The DEP force can attract or move cells away. The constant cells are captured in the area with the electrode and prove a quantitative counting area.

According to the invention, the "endothelium-like or epithelium-like cells" refer to endothelial cells or epithelium cells and their analogues. Preferably, the endothelium-like or epithelium-like cells are blood vessel cells, lymph vessel cells, oral epithelium cells or human umbilical vein endothelial cells.

According to the invention, the "inflammation-inducing agent" refers to agents that can induce an inflammation reaction. Preferably, the inflammation-inducing agent is cytokin, growth factor, surface protein or interleukin. Preferably, the inflammation-inducing agent is tumor necrosis factor or interleukin. More preferably, the inflammation-inducing agent is tumor necrosis factor-α, interleukin-1 (IL-1), IL-2, IL-6, IL-8, IL-1β, interferon-gamma (IFN-gamma), interferon-alpha (IFN-alpha) or TNF-alpha.

According to the invention, "white blood cells" refer to cells of the immune system defending the body against both infectious disease and foreign materials. In one embodiment, the white blood cells include neutrophils, eosinophils, basophils, lymphocytes, monocytes and macrophage. Preferably, the white blood cells are neutrophils and macrophages. White blood cells migrate toward sites of inflammation and they attach to foreign substances to kill them. According to the invention, the white blood cells attach to living, nucleus-containing heterogenic cells. After an inflammation reaction is induced according to the invention, the white blood cells move to the endothelium-like or epithelium-like cells and attach thereto. In one embodiment of the invention, the white blood cells used in the method of the invention may originally exist in the body fluid sample. In another embodiment of the invention, the white blood cells are added and applied in the invention.

According to the invention, the "body fluid sample" or "the serum-containing sample" may be derived from any biological source, such as a physiological fluid, including whole blood; ascites; saliva, urine; synovial fluid; peritoneal fluid; amniotic fluid; cerebrospinal fluid; serosal fluid; spinal fluid and other constituents of the body which may contain tumor cells. If the sample contains tumor cells, they can be captured by the white blood cells when employing the kit and method of the invention because the tumor cells are nucleus-containing heterogenic cells that can be identified and recognized by white blood cells. According to one embodiment of the invention, the body fluid sample or the serum-containing sample may be pre-treated prior to use by the method and kit of the invention so that the sample is in a physiological condition to facilitate capture of living tumor cells and use of living cells in the method and kit of the invention. According to another embodiment of the invention, the method can further comprise a step of pre-treating a biological sample to form a serum-containing sample. According to the invention, the biological sample is any kind of body sample; preferably, the biological sample is bone marrow aspirates, bone marrow homogenates, lymphoid tissue homogenates or tissue homogenates. Preferably, the biological sample is a solution containing tissue. Preferably, the sample is pre-diluted more than 10 times. In one embodiment, the sample volume used in the invention ranges from about 5 to about 30 mL. Preferably, the sample volume is from about 5 to about 25 mL, about 5 to about 20 mL, about 5 to about 15 mL, about 5 to about 10 mL, about 10 to about 25 mL, about 15 to about 25 mL, about 10 to about 20 mL or 15 mL to 20 mL.

According to the invention, the tumor cells in the body fluid sample or the serum-containing sample are derived or secreted from tumor tissues. Preferably, the tumor cells are circulating tumor cells. According to the invention, after the tumor cells are captured, they can be further harvested by methods known in the art. For example, tumor cells or their fragments are extensively washed in large spectrum antibiotics and antifungic solutions in completed DMEM (6-7 washes) to achieve an aseptic level compatible with standard cell culture conditions. Then, the cells or fragments are cut into small pieces of 1 to 2 mm$^3$. These pieces are seeded in 6-well plates pre-coated with PolyHEMA with 2 mL of complete medium. Tumor fragments are cultivated for 2 d, and then the medium is retrieved and replaced by medium alone or drug-containing medium for 24 h. The drug used is the topoisomerase-I inhibitor metabolite SN-38 (7 ethyl 10 hydroxycamptotecin), which is the active metabolite of camptothecin at 10-5 mM/l, a concentration similar to that observed in tumors after i.v. administration of camptothecin in humans. At the end of this period, a washout is performed to eliminate the drug, and medium is added for 72 h.

The kit of the invention is used to practice the method of the invention. According to the invention, the kit includes (a) a solid support, (b) endothelium-like or epithelium-like cells that are attached to the solid support, (c) white blood cells that are attached to the cells of (b), and (d) one or more inflammation-inducing agent. Each of the above materials of (a), (b), (c) and (d) of the kit is placed in a separate container such as a vial, tube, or the like. That is, each of the containers comprises one of the separate materials to be used in the assay. The kit may further include a set of instructions for using the kit to conduct the intended assay for capturing tumor cells in a body fluid sample.

In the kits and methods of the invention, the endothelium-like or epithelium-like cells attached to a solid support can be induced to generate inflammation reaction. The inflammation reaction is induced by adding one or more inflammatory-inducing agents. After inflammation is induced, white blood cells used in the kits and methods of the invention will migrate and attach to the inflamed cells. Since white blood cells will capture living, nucleus-containing heterogenic cells, after a body fluid sample is added, the tumor cells in the sample will be captured by the white blood cells. However, non-living cells, cell fragments and other contaminants in the sample will not be captured by the white blood cells. By using the kit and method of the invention, living tumor cells in a body fluid sample or a serum-containing sample can be separated for further identification using methods known in the art such as real time PCR or flowcytometry after culturing them (Barrett D L, Jensen R H, King E B, Dean P N, Mayall B H. Flow cytometry of human gynecologic specimens using log chromomycin A:, fluorescence and log 90° light scatter. J Histochem Cytochem 27(1):573-578, 1979; Darzynkiewicz Z: Acridine orange as a molecular probe in studies of nucleic acids in situ. In: Flow Cytometry and Sorting, Melamed M R, Mullaney P F, Mendelsohn M L (eds). John Wiley & Sons, New York, 1979, pp 285-316; Frost J K, Tyrer H W, Pressman N J, Albright C D, Vansickel M H, Gill G W: Automatic cell identification and enrichment in lung cancer. I. Light scatter and fluorescence parameters. J Histochem Cytochem 27545-551, 1979; and Frost J K, Tyrer H W, Pressman N J, Adams L A, Vansickel M H, Albright C D, Gill G W, Tiffany S M: Automatic cell identification and enrichment in lung cancer. In. Light scatter and two fluorescence parameters. J Histochem Cytochem 27557-559, 1979).

EXAMPLES

Example 1

Attachment of Tumor Cells to Epithelium Cells

A glass plate with gelatin-modified surface was placed at the bottom of a Petri dish and then about 50,000 human embryonic kidney 293T (HEK-293T) endothelial cells or human umbilical vein endothelial cells (HUVEC) were seeded on the glass plate. After adding DMEM and M199 mediums to the Petri dishes, the cells were cultivated at 37° C., 5% $CO_2$ for 24 hours. Subsequently, the DMEM and M199 mediums were removed from the Petri dishes and the Petri dishes were washed with PBS buffer. Subsequently, the fresh DMEM and M199 mediums were added to the Petri dish. 50 ng of inflammation-inducing agents such as interleukin-1β (IL-1β) and tumor necrosis factor-alpha (TNF-α) were added to the Petri dishes to induce inflammation reaction of HEK-293T and HUVEC for 24 hours. The expression level of interleukin-6 (IL-6) was measured by Enzyme-linked immunoassay (ELISA). If the expression level of IL-6 is higher than 30 ng/ml, an inflammation reaction occurs. Alternatively, the expression level of IL-6 can be detected by Flow Cytometry. The ICAM antibodies attached to fluorescein isothiocyanate (FITC) were added to the Petri dishes to capture ICAM-1 (inter-cellular adhesion molecule 1) which was induced by IL-1 and TNFα and expressed by the endothelium. The FITC fluorescein was measured by Flow Cytometry. If the expression level of ICAM-1 is higher than 10 ng/ml, an inflammation reaction occurs.

The tumor cells, liver cancer cells hepG2, were transfected with green fluorescence protein (GFP). The hepG2 cells with GFP were added to the Petri dishes. After shaking for 10 minutes, 15 ml PBS buffer was added for washing. After washing 3 times, the Petri dishes were examined using optical microscope and fluorescence microscopy, respectively.

FIG. 1 is directed to optical microscope photographs showing the attachment of tumor cells to the epithelium cells with (FIG. 1(B)) or without (FIG. 1(A)) inducing an inflammation reaction on the epithelium cells by using IL-1β. In FIG. 1(A), after washing, no hepG2 cells were attached to the epithelium cells, whereas in FIG. 1(B), after washing, it can be seen that hepG2 cells were attached to the epithelium cells.

Figure 2:
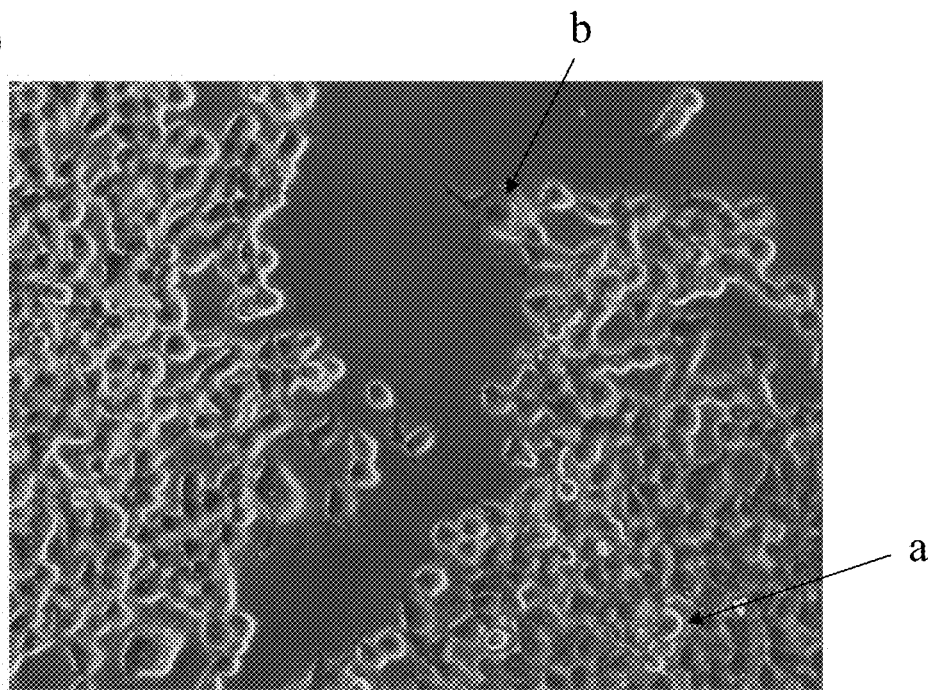
FIG. 2 is directed to optical microscope photographs showing the attachment of tumor cells to the epithelium cells after inducing an inflammation reaction on the epithelium cells by using either IL-1β (FIG. 2.(A)) or TNF-alpha (FIG. 2(B)). The "a" in the figure represents tumor cells (hepG2 cells) and the "b" represents epithelium cells.
Figure 2:
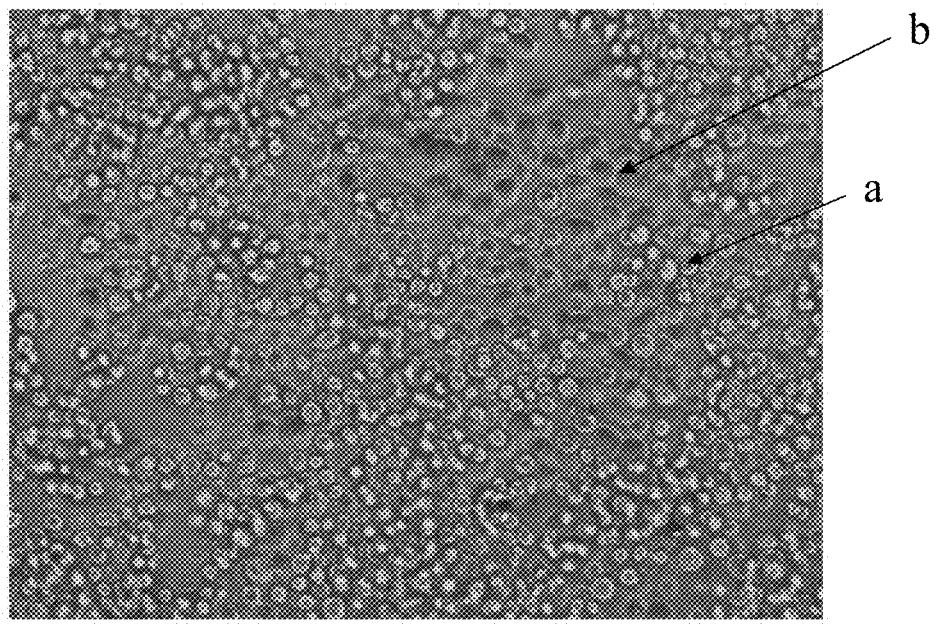

FIG. 2 is directed to optical microscope photographs showing the attachment of tumor cells to the epithelium cells after inducing an inflammation reaction on the epithelium cells by using IL-1β (FIG. 2.(A)) and TNF-alpha (FIG. 2(B)). In both FIGS. 2(A) and (B), after washing, it can be seen that hepG2 cells were attached to the epithelium cells. After an inflammation reaction was induced by either IL-1β or TNF-alpha, the epithelium cells can capture the tumor cells.

Example 2

Attachment of Tumor Cells to White Blood Cells (neutrophils) After Inducing an Inflammation Reaction on the Epithelium Cells A glass plate with gelatin-modified surface was placed at the bottom of a Petri dish and then about 50,000 human embryonic kidney 293T (HEK-293T) endothelial cells or human umbilical vein endothelial cells (HUVEC) were seeded on the glass plate. After adding DMEM and M199 mediums to the Petri dishes, the cells were cultivated at 37° C., 5% $CO_2$ for 24 hours. Subsequently, the DMEM and M199 mediums were removed from the Petri dishes and the Petri dishes were washed with PBS buffer. Subsequently, the fresh DMEM and M199 mediums were added to the Petri dish. 50 ng of inflammation-inducing agents such as interleukin-1β (IL-1β) and tumor necrosis factor-alpha (TNF-α) were added to the Petri dishes to induce inflammation reaction of HEK-293T and HUVEC for 24 hours. The expression level of interleukin-6 (IL-6) was measured by Enzyme-linked immunoassay (ELISA). If the expression level of IL-6 is higher than 30 ng/ml, an inflammation reaction occurs. Alternatively, the expression level of IL-6 can be detected by Flow Cytometry. The ICAM antibodies attached to fluorescein isothiocyanate (FITC) were added to the Petri dishes to capture ICAM-1 (inter-cellular adhesion molecule 1) which was induced by IL-1 and TNFα and is expressed by the endothelium. The FITC fluorescein was measured by Flow Cytometry. If the expression level of ICAM-1 is higher than 10 ng/ml, an inflammation reaction occurs.

Neutrophils were added to the Petri dishes and they attached to the inflamed HEK-293T and HUVEC cells. The tumor cells, liver cancer cells hepG2, were transfected with green fluorescence protein (GFP). The hepG2 cells with GFP were added to the Petri dishes. After shaking 10 minutes, 15 ml PBS buffer was added for washing. After washing 3 times, the Petri dishes were examined using optical microscope and fluorescence microscopy, respectively.

Figure 3:
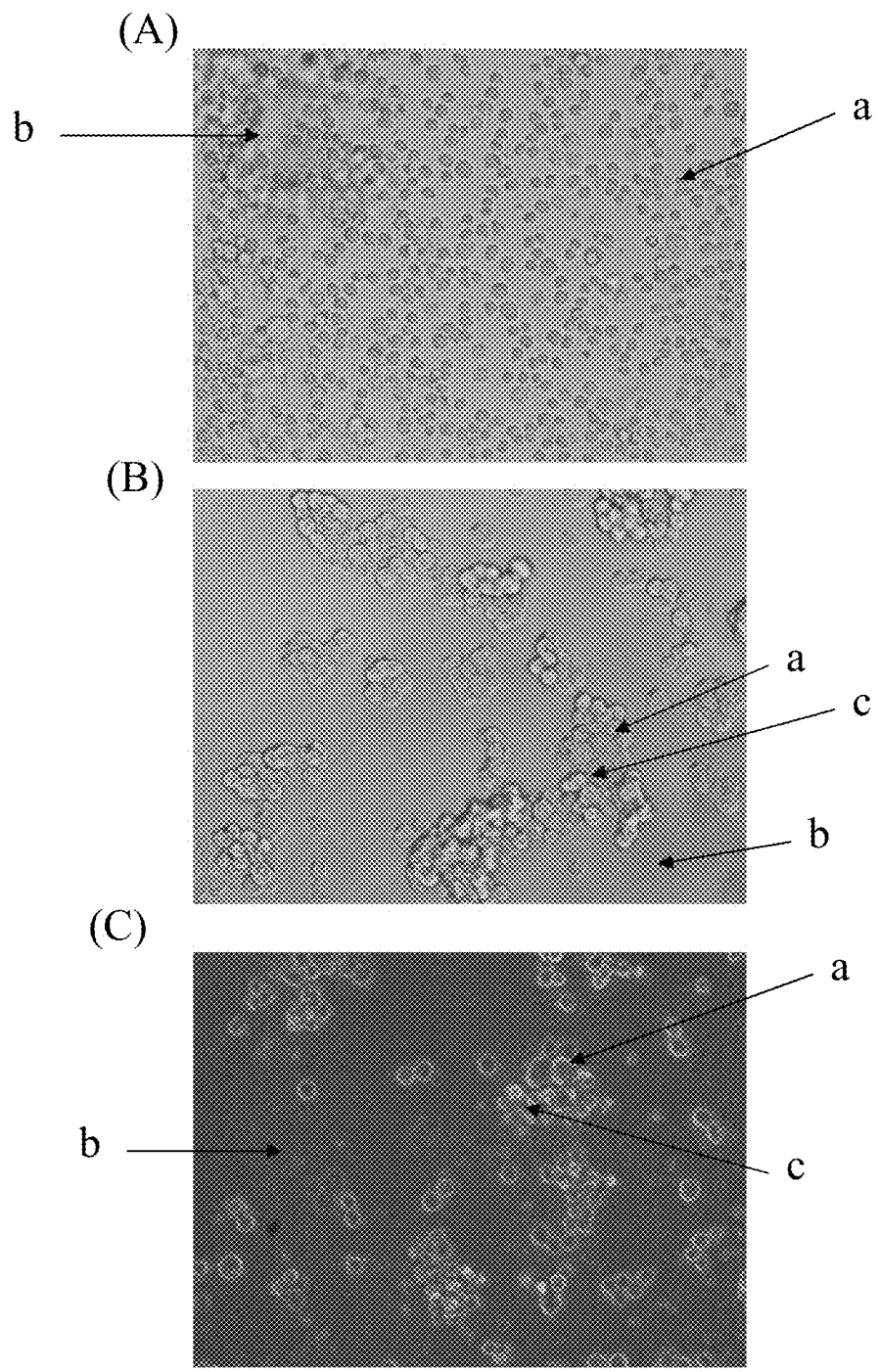
FIG. 3 is directed to optical microscope photographs showing the attachment of tumor cells to the white blood cells (neutrophils) after inducing an inflammation reaction on the epithelium cells by using either IL-1β (FIG. 3(B)) or TNF-alpha (FIG. 3(C)).

FIG. 3 is directed to optical microscope photographs showing the attachment of tumor cells to the white blood cells (neutrophils) after inducing an inflammation reaction on the epithelium cells by using IL-1β (FIG. 3(B)) and TNF-alpha (FIG. 3(C)). FIG. 3(A) is a control group wherein no white blood cells were added. In FIGS. 3(B) and (C), the hepG2 cells attached to the neutrophils and clustered together, whereas in FIG. 3(A) the hepG2 cells randomly distributed in the Petri dish.

Example 3

Capture of Tumor Cells in the Presence of Red Blood Cells

A glass plate with gelatin-modified surface was placed at the bottom of a Petri dish and then about 50,000 human embryonic kidney 293T (HEK-293T) endothelial cells or human umbilical vein endothelial cells (HUVEC) were seeded on the glass plate. After adding DMEM and M199 mediums to the Petri dishes, the cells were cultivated under 37° C., 5% $CO_2$ for 24 hours. Subsequently, the DMEM and M199 mediums were removed from the Petri dishes and the Petri dishes were washed with PBS buffer. Subsequently, the fresh DMEM and M199 mediums were added to the Petri dish. 50 ng of inflammation-inducing agents such as interleukin-1β (IL-1β) and tumor necrosis factor-alpha (TNF-α) were added to the Petri dishes to induce inflammation reaction of HEK-293T and HUVEC for 24 hours. The expression level of interleukin-6 (IL-6) was measured by Enzyme-linked immunoassay (ELISA). If the expression level of IL-6 is higher than 30 ng/ml, an inflammation reaction occurs. Alternatively, the expression level of IL-6 can be detected by Flow Cytometry. The ICAM antibodies attached to fluorescein isothiocyanate (FITC) were added to the Petri dishes to capture ICAM-1 (inter-cellular adhesion molecule 1) which was induced by IL-1 and TNFα and is expressed by the endothelium. The FITC fluorescein was measured by Flow Cytometry. If the expression level of ICAM-1 is higher than 10 ng/ml, an inflammation reaction occurs.

Neutrophils were added to the Petri dishes and they attached to the inflamed HEK-293T and HUVEC cells. The question of whether the presence of red blood cells affects the capture of tumor cells by white blood cells was evaluated. The whole blood testing samples containing the hepG2 cells were collected. The blood samples were not diluted or diluted 10 times and 1000 times, respectively. Then Wright's stain was added to the blood samples to label the hepG2 cells contained therein. After staining, the blood samples were added to the Petri dishes. Subsequently, the Petri dishes were examined using optical microscope.

In addition, the whole blood testing samples containing the hepG2 cells were collected and frozen for 30 minutes. The blood samples were not diluted or diluted 1000 times. Then Wright's stain was added to the blood samples to label the hepG2 cells contained therein. After staining, the blood samples were added to the Petri dishes. Subsequently, the Petri dishes were examined using optical microscope.

Figure 4:
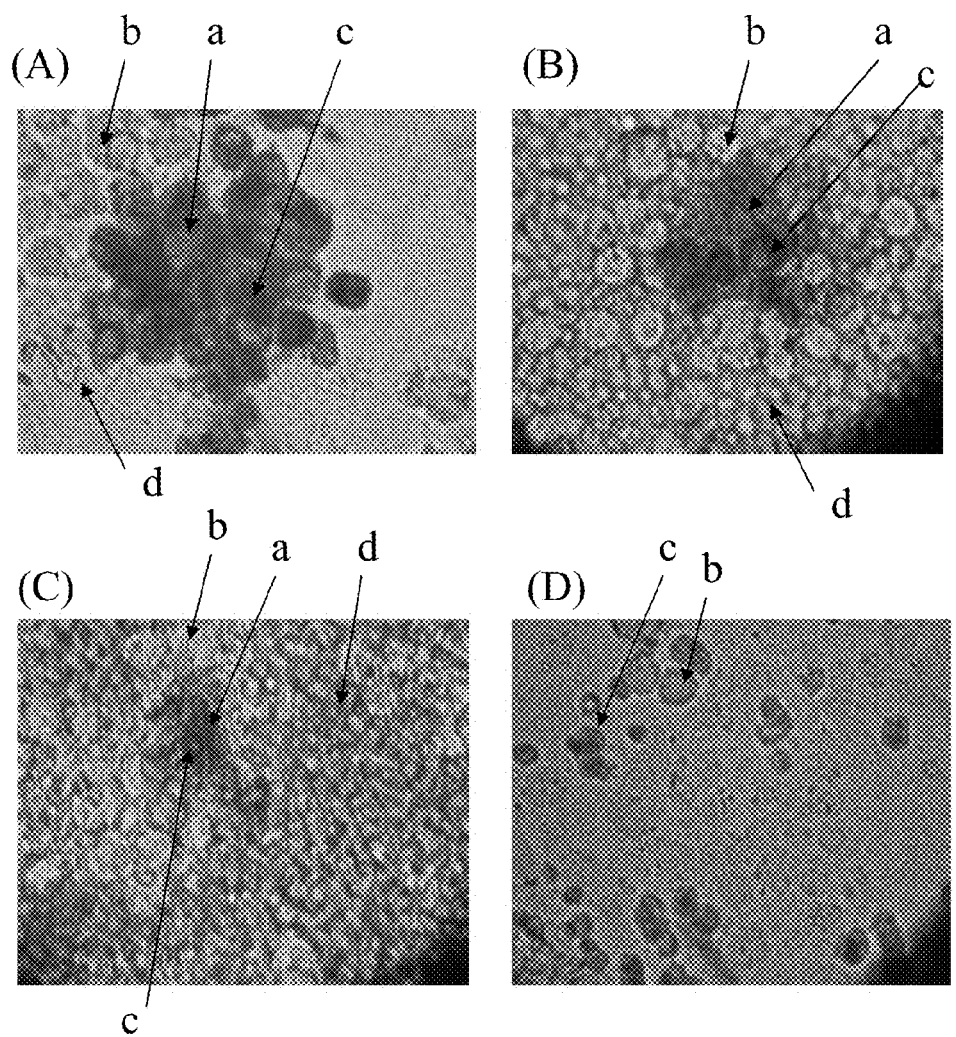
FIGS. 4(A) and 4(B) show photographs of whole blood samples containing the living hep G2 cells in a dilution of 10 times and 1,000 times, respectively.
FIG. 4(C) shows a photograph of the whole blood sample containing the living hep G2 cells without dilution and FIG. 4(D) shows a photograph of the whole blood sample containing the dead hep G2 cells in a dilution of 1,000 times. The "a" in the figure represents tumor cells (hepG2 cells); the "b" represents epithelium cells; the "c" represents white blood cells (neutrophils); and the "d" represents red blood cells.

FIG. 4 is directed to the optical microscope photographs showing the capture of living or dead tumor cells in the whole blood samples without or with dilution 10 times or 1,000 times. FIGS. 4(A) and 4(B) show the photographs of the whole blood samples containing the living hep G2 cells in a dilution of 10 times and 1,000 times, respectively. FIG. 4(C) shows the photograph of the whole blood sample containing the living hepG2 cells without dilution and FIG. 4(D) shows the photograph of the whole blood sample containing the dead hepG2 cells in a dilution of 1,000 times. This proves that the presence of red blood cells did not affect the capture of the tumor cells by neutrophils.

What is claimed is:

1. A method for the capture of circulating tumor cells in a body fluid sample or a serum-containing sample, comprising the following steps:
    (a) attaching endothelium or epithelium cells on a solid support,
    (b) adding white blood cells to the attached endothelium or epithelium cells (a) for capturing the circulating tumor cells, wherein the white blood cells are neutrophils, eosinophils, basophils, lymphocytes, monocytes or macrophages;
    (c) adding one or more inflammation-inducing agent to induce an inflammation reaction on said attached endothelium or epithelium cells and white blood cells, wherein the inflammation-inducing agent is a tumor necrosis factor or an interleukin; and
    (d) adding a body fluid sample or a serum containing sample to the solid support whereby the white blood cells and the endothelium or epithelium cells capture circulating tumor cells contained in the body fluid sample or the serum-containing sample, and wherein the body fluid sample or the serum-containing sample is pre-diluted more than 10 times.

2. The method of claim 1, which further comprise a step of pre-treating the body fluid sample or the serum-containing sample prior to adding in step (d) of the method so that the sample is in a physiological condition.

3. The method of claim 1, which further comprise prior to adding in step (d) of the method, a step of pre-treating a biological sample to a serum-containing sample.

4. The method of claim 3, wherein the biological sample is bone marrow aspirates, bone marrow homogenates, lymphoid tissue homogenates or tissue homogenates.

5. The method of claim 1, which further comprises after step (d), a step of harvesting the captured circulating tumor cells.

6. The method of claim 1, wherein the solid support is hydrophilic.

7. The method of claim 1, wherein the solid support is composed of an organic polymer selected from the group consisting of nitrocellulose membrane, nylon membrane, polystyrene, polyethylene, polypropylene, polyfluoroethylene, polyethyleneoxy, and polyacrylamide, as well as co-polymers and grafts thereof.

8. The method of claim 1, wherein the solid support is composed of inorganic materials selected from the group consisting of glass, silica and reverse-phase silica.

9. The method of claim 1, wherein the solid support is in the form of a bead, a sphere, a particle, a granule, a gel, or a surface.

10. The method of claim 1, wherein the solid support is in the form of a well, a depression or a vessel.

11. The method of claim 1, wherein the solid support is a Petri dish or a microtiterplate.

12. The method of claim 1, wherein the solid support possesses electrode(s) thereon.

13. The method of claim 12, wherein the electrode is composed of indium tin oxide (ITO), carbon nanotube, silicon, or titanium oxide.

14. The method of claim 1, wherein the inflammation-inducing agent is tumor necrosis factor-$\alpha$, interleukin-1 (IL-1), IL-2, IL-6, IL-8, IL-1$\beta$, interferon-gamma (IFN-gamma), interferon-alpha (IFN-alpha) or TNF-alpha.

15. The method of claim 1, wherein the white blood cells are neutrophils or macrophages.

16. The method of claim 1, wherein the body fluid sample or the serum-containing sample is whole blood, ascites, saliva, urine, synovial fluid, peritoneal fluid, amniotic fluid, cerebrospinal fluid, serosal fluid or spinal fluid.

17. The method of claim 1, wherein the sample volume of the body fluid sample ranges from about 5 to about 30 mL.

18. The method of claim 1, wherein the sample volume of the body fluid sample ranges from 5 to about 25 mL.

* * * * *